(12) United States Patent
Kuhn et al.

(10) Patent No.: US 11,729,357 B2
(45) Date of Patent: Aug. 15, 2023

(54) IMAGE RECORDING ARRANGEMENT, ASSOCIATED USE AND METHOD FOR COMMISSIONING AN IMAGE RECORDING ARRANGEMENT

(71) Applicant: Scholly Fiberoptic GmbH, Denzlingen (DE)

(72) Inventors: Matthias Kuhn, Freiburg (DE); Alexander Kohler, Freiburg (DE)

(73) Assignee: Scholly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 16/411,289

(22) Filed: May 14, 2019

(65) Prior Publication Data

US 2019/0356839 A1 Nov. 21, 2019

(30) Foreign Application Priority Data

May 15, 2018 (DE) .......................... 102018111645.4

(51) Int. Cl.
*H04N 5/232* (2006.01)
*H04N 7/18* (2006.01)
(Continued)

(52) U.S. Cl.
CPC ......... *H04N 7/183* (2013.01); *A61B 1/00006* (2013.01); *A61B 1/00009* (2013.01);
(Continued)

(58) Field of Classification Search
CPC ............... H04N 5/23203; H04N 7/183; H04N 2005/2255; A61B 1/00006;
(Continued)

(56) References Cited

U.S. PATENT DOCUMENTS

2005/0165274 A1\* 7/2005 Abe .......................... A61B 1/04
600/117
2013/0329183 A1\* 12/2013 Blum ...................... G06F 3/011
351/158

(Continued)

*Primary Examiner* — John W Miller
*Assistant Examiner* — Omer Khalid
(74) *Attorney, Agent, or Firm* — Volpe Koenig

(57) ABSTRACT

In order to reduce costs for endoscopic examinations and to enable new operating concepts, an image recording arrangement is provided in which an adapter that enables bi-directional communication between a camera control unit and an image generation unit which has an image sensor. A standardized data interface is configured between the camera control unit and the adapter. The adapter is defined for use with a specific type of image generation unit. Accordingly, the adapter has a communication apparatus which translates control and adjustment commands transmitted by the camera control unit into a format processable by the image generation unit and provides image data from the image sensor in a format processable by the camera control unit. The camera control unit can therefore access, control and adjust the image generation unit and can display image data from the image generation unit without adaptation to the image generation unit connected to the adapter and therefore without knowledge of said image generation unit.

20 Claims, 3 Drawing Sheets

(51) Int. Cl.
*A61B 1/045* (2006.01)
*A61B 1/00* (2006.01)
*H04N 5/225* (2006.01)
*H04N 23/66* (2023.01)
*H04N 23/50* (2023.01)

(52) U.S. Cl.
CPC ...... *A61B 1/00016* (2013.01); *A61B 1/00121* (2013.01); *A61B 1/045* (2013.01); *H04N 23/66* (2023.01); *A61B 1/0004* (2022.02); *H04N 23/555* (2023.01)

(58) Field of Classification Search
CPC ............ A61B 1/00009; A61B 1/00016; A61B 1/00039; A61B 1/00121; A61B 1/045
See application file for complete search history.

(56) References Cited

U.S. PATENT DOCUMENTS

| | | | |
|---|---|---|---|
| 2015/0077926 A1* | 3/2015 | Schneider | H02J 7/0044 361/679.41 |
| 2015/0293877 A1* | 10/2015 | Liang | G06F 13/4068 710/33 |
| 2017/0105129 A1* | 4/2017 | Teplin | H04L 41/0806 |
| 2017/0336579 A1* | 11/2017 | Sanandajifar | G02B 6/00 |
| 2019/0201104 A1* | 7/2019 | Shelton, IV | A61B 1/00055 |

* cited by examiner

IMAGE RECORDING ARRANGEMENT, ASSOCIATED USE AND METHOD FOR COMMISSIONING AN IMAGE RECORDING ARRANGEMENT

INCORPORATION BY REFERENCE

The following documents are incorporated herein by reference as if fully set forth: German Patent Application No. 10 2018 111 645.4, filed May 15, 2018.

BACKGROUND

The invention relates to an image recording arrangement comprising an image generation unit with an image sensor, a camera control unit and an adapter for setting up a bidirectional data connection between the image sensor and the camera control unit. The invention furthermore relates to the use of an image recording arrangement of this type and a method for the commissioning thereof. Finally, the invention relates to an image recording module and an image recording series.

Image recording arrangements as described above are known, wherein image data are transmittable from the image sensor, which may be disposed, for example, in a distal end area of the image generation unit, to the camera control unit, and the camera control unit is configured to control the image sensor. The image generation unit can be designed, in particular, as an endoscope.

The term image data can be understood here, in particular, to mean already-processed digital image data or video signals or unprocessed analog or digital output signals from the image sensor.

In the known systems, it has become customary to implement the data connection via a cable, wherein a connector by which the cable can be connected to the camera control unit is configured at the proximal end of the cable.

SUMMARY

The design of connectors of this type has proven to be complex, particularly if the image generation unit has to be sterilized, as required in medical applications. The invention aims to provide a simpler solution here. Furthermore, the usage characteristics of a module consisting of a camera control unit and a plurality of different image generation units to be used with the camera control unit are also intended to be improved.

One or more features are provided according to the invention in an image recording arrangement to achieve these objects. In particular, in order to achieve the object, it is thus provided according to the invention in an image recording arrangement of the aforementioned type that the adapter has a communication apparatus for transmitting control signals to the image sensor and for receiving output signals from the image sensor. The communication apparatus is defined here specifically for the image sensor, if necessary also for the image generation unit as a whole, even before a connection is first set up between the adapter and the camera control unit. This specific definition may, in particular, be such that the communication apparatus can communicate bi-directionally with the image sensor without further adaptations and/or immediately following the set-up of a connection to the image sensor, i.e., for example, can access and control the image sensor and can read and/or process data and/or signals from the image sensor.

The communication apparatus can thus be defined, in particular, specifically for the image sensor, if necessary also for the image generation unit as a whole, even before a connection is first set up between the adapter and the image sensor of the image generation unit.

The image generation unit of the image recording arrangement may, for example, be an endoscope with an image sensor or with a plurality of image sensors. The image generation unit can also be formed by a camera head to which a conventional, in particular non-electronic, endoscope or, for example, an optical probe is connected.

Finally, the image generation unit may be an, in particular, simply designed and/or electronic, single-use endoscope. A single-use endoscope can be understood, for example, to mean an endoscope which is designed for a one-off use only and is not therefore sterilized or sterilizable.

Due to the bi-directionality of the data connection set up by the adapter between the image generation unit, in particular its image sensor, and the camera control unit, image data can be transmitted in one direction from the image sensor to the camera control unit and control/adjustment commands can be transmitted in the opposite direction from the camera control unit to the image sensor and/or the image generation unit. A control loop, in particular, can thus be configured between the image generation unit, in particular its image sensor, and the adapter and/or the camera control unit.

An image recording arrangement according to one or more features of the invention thus offers the advantage that the camera control unit can transmit standardized control/adjustment commands, i.e., in particular, control/adjustment commands which are independent from the type of the image generation unit/endoscope/image sensor, to the adapter in order to thus control/adjust the image generation unit/image sensor. In one new development of the image generation unit, only the adapter, but not the camera control unit, must therefore be adapted. This offers advantages for the user, since said user can continue to use a camera control unit which is already in use, even with newly developed image generation units.

Unlike the image recording arrangements known in the prior art, the solution according to the invention can be designed as both downward-compatible and upward-compatible. The camera control unit does not "see" the image generation unit, but only the adapter.

The configuration of an adapter according to the invention therefore offers the advantage that an existing camera control unit is particularly simply adaptable to a new image generation unit through exchange of the adapter or through reprogramming of the adapter, in particular its communication apparatus.

On the other hand, however, an existing image generation unit can also be adapted by an adapter according to invention to a new camera control unit which has, for example, a new set of control commands and transmits said control commands to the adapter. For this purpose, corresponding adaptations can be performed in the camera apparatus of the adapter, or a new adapted adapter can be designed.

The adapter, in particular its communication apparatus, can be reprogrammable, for example by an external computer or the camera control unit. The adapter can be adapted to a new communication apparatus and/or to a new image generation unit through the reprogramming. In such cases also, the adapter can furthermore be defined specifically for the image sensor even before a connection is first set up between the adapter and the camera control unit; however, due to the undertaken reprogramming, the adapter can be enabled, for example, to convert new control commands from a new camera control unit into control signals which are adapted to an existing image generation unit or to its image sensor or to its further sensor.

According to the invention, expensive and sensitive electronic components, such as, for example, a data or signal conversion unit, can furthermore be translocated out of the image generation unit into the adapter according to the invention which does not need to be reprocessed, since it can be disposed outside the sterile area of the image generation unit. These electronic components can therefore be used repeatedly without processing. Correspondingly, the requirements to be imposed on the adapter in terms of design and impermeability can also be substantially reduced.

An image generation unit to be used with an adapter designed according to the invention can furthermore be of very simple design. In a minimal configuration, an image generation unit of this type comprises only one image sensor, associated imaging optics and necessary peripherals such as, for example, a voltage supply; if necessary, simple electronics for amplifying the (typically analog) output signals from the image sensor can also be configured.

The fact that the processing of, in particular analog, output signals from the image sensor can be performed according to the invention in the adapter and not, for example, in a downstream camera control unit offers further advantages in that the adapter can thus perform not only a possibly necessary mechanical, but also the electrical, adaptation between the image generation unit and the camera control unit. Existing high-quality camera control units can therefore be used flexibly and therefore economically in the image recording arrangement.

A further advantage is that a power dissipation from electronics, which normally occurs in the image generation unit, is translocated into the adapter. A critical heating of the image generation unit can thus be counteracted, this being critical, particularly in medical applications.

The object can also be achieved according to the invention by further advantageous designs as discussed in detail below and in the claims.

As well as image sensors, for example, the image generation unit can have at least one further sensor, for example at least one pressure, temperature or position sensor. In such a case, it is favorable for a simplified use of the image generation unit if the communication apparatus of the adapter is configured to transmit control signals to the at least one further sensor and to receive output signals or data from the at least one further sensor. The at least one further sensor can thus be readable via the adapter and/or the camera control unit.

By using an adapter of this type, the data connection between the at least one further sensor of the image generation unit and the camera control unit can also be configured as bidirectional. A control loop, in particular, can thereby be configured between the at least one further sensor and the adapter and/or the camera control unit. The further sensor can thus be read and/or adjusted in a particularly simple manner by an existing camera control unit.

In order to adapt the adapter for use with a wide variety of different image generation units, in particular endoscope/image sensor types or to new further sensors in the image generation unit, it can be provided that the adapter has an interface for the reprogramming of its communication apparatus. The adapter can be defined via this interface specifically for the image sensor/image generation unit/further sensor to be used even before the data connection is first set up between the image sensor/image generation unit/further sensor and the camera control unit.

The image generation unit can be designed accordingly, in particular, in such a way that the image generation unit and/or the image sensor and/or the further sensor is/are usable as intended only together with the adapter. The adapter, but not the image generation unit can, for example, have the electronics necessary for the processing and forwarding of the output signals from the image sensor and/or from the further sensor. This approach is highly advantageous, particularly in the case of single-use endoscopes, since electronics can be used sparingly in the endoscope and the latter can therefore be designed more economically.

Single-use endoscopes are of interest, in particular, for flexible endoscopes, since the latter are very difficult to sterilize. The elimination of the need for sterilization of the endoscope due to the only single use thereof can therefore be highly advantageous in specific applications. The invention makes an important contribution here, since the use of single-use endoscopes is enabled at lower costs, given that electronics can be translocated into the adapter.

According to one further advantageous design, the communication apparatus can alternatively be designed as invariable. In this case, the adapter is usable only with a single type of image generation unit/a single endoscope/image sensor/further sensor type. It is advantageous that the communication apparatus of the adapter can be designed in this case as simpler and therefore more economical.

Through the translocation of (high-quality) electronics, such as, for example, FPGAs or driver circuits, out of the image generation unit, for example out of the camera head of an endoscope, into the adapter according to the invention, it is possible, in particular, to dispense largely or even entirely with signal processing in the image generation unit. It therefore becomes possible to manufacture the image generation unit at hitherto unattainable costs. This approach is of great interest, particularly for the development of single-use endoscopes. According to one further design, it can therefore be provided that the endoscope of the image recording arrangement is designed for single use and/or is a non-autoclavable single-use endoscope.

Due to the specific nature of the adapter according to the invention, the camera control unit can access, control and adjust the image sensor and/or the image generation unit, particularly if the camera control unit does not know which image generation unit/image sensor is currently connected to the adapter. In particular, no identification information (ID) therefore needs to be transmitted from the adapter to the camera control unit. One development of the invention therefore provides that the image recording arrangement is configured in such a way that the camera control unit can have a controlling/adjusting effect on the image generation unit and/or the image sensor and/or the at least one further sensor as soon as the adapter sets up the data connection, without knowledge of the image generation unit and/or image sensor and/or at least one further sensor then connected to the adapter. The image generation unit can, for example, have an illumination apparatus which can be controlled via the camera control unit using the adapter.

If a new image generation unit, for example with a new type of sensor or a new type of data format or other new characteristics or new further sensors, is intended to be used with an existing camera control unit, the required alignment can be performed by means of an adapter according to the invention. In this case, the adapter performs the adaptation of the image generation unit/image sensor/further sensor to existing requirements of the camera control unit. The adapter can furthermore be designed so that an existing camera control unit can control and adjust a new image generation unit/image sensor/further sensor. For this purpose, according to one further design, the adapter has a data interface for receiving control commands transmitted by the camera control unit and for transmitting image data from the image sensor and/or other data from the further sensor to the camera control unit in a format processable by the camera control unit. Both the control commands and the image data can be exchanged, particularly in digital form, between the adapter and the camera control unit.

A further advantageous design provides that the communication apparatus is defined in terms of its electronic characteristics specifically for the reception of output signals from a specific image sensor type and/or from a specific further sensor type and/or for the generation of control signals for a specific image generation unit, in particular for a specific image sensor type and/or a specific further sensor type. It can be provided, in particular, that these electronic characteristics are invariable. It is also advantageous with designs of this type that a transmission of identification information or the like to the adapter or from the adapter to the camera control unit is superfluous.

A further possible design provides that the communication apparatus can convert the control commands from the camera control unit only into control signals which are processable by the image sensor/further sensor. It is advantageous that, through the exchange of adapters according to the invention, different image generation units or different image sensors or different further sensors are controllable with the same camera control unit; the camera control unit itself does not therefore have to be readapted each time.

By the aforementioned data interface, the adapter is enabled to convert a signal transmitted by the image sensor into a format suitable for the camera control unit. In medical applications, for example, in which two endoscopes are intended to be used simultaneously, two or more adapters according to the invention can also be connected to the camera control unit so that a plurality of endoscopes are simultaneously usable, i.e., in particular, are controllable and adjustable, with the camera control unit.

Alternatively, a single adapter can also be used which has a plurality of interfaces for connecting image generation units.

An image recording arrangement according to the invention can therefore have, in particular, a plurality of image generation units and, if necessary, a plurality of adapters. If a plurality of adapters are used, the camera control unit can have a necessary number of interfaces for connecting a plurality of adapters. With this approach, only one single camera control unit is to be used to control a plurality of image generation units, and a uniform operating concept can be retained which substantially simplifies the operation, for example, of different endoscopes, for the user.

The communication apparatus can be configured, in particular, to receive analog and/or digital output signals from the image sensor/further sensor. The data interface can also be designed for the transmission of analog and/or digital data.

An adapter designed according to the invention can be connected, for example, via a cable (e.g. USB or analog video interface) or wirelessly, for example via a radio link (e.g. WLAN), to the image generation unit/image sensor. In an image recording arrangement according to the invention, the adapter can thus be arrangeable at a distance from the image generation unit while the data connection is maintained between the image sensor/image generation unit and the camera control unit. The adapter can therefore, in particular, be removable from a sterile area of the image generation unit. This has advantages, particularly in medical applications, since the adapter does not necessarily need to be sterilizable.

The adapter can therefore be designed, in particular, as non-sterilizable, for example non-autoclavable. The adapter can therefore be manufactured substantially more simply and economically. It is obviously also possible for the adapter to be used with image generation units which are processed after one use through sterilization for a further use (referred to as "multi-use endoscopes").

The adapter can be designed, in particular, in such a way that it is detachably connectable to the camera control unit, i.e., for example, is insertable or pluggable therein. An, in particular first, plug-in connection between the adapter and the camera control unit can preferably be configured for this purpose. This plug-in connection can, in particular, form the data interface described above.

Alternatively, however, the data interface between the adapter and the camera control unit can also be designed as a wireless link.

According to one further advantageous design, it can be provided that the adapter has an interface on the image side, designed, in particular, as a second plug-in connection, for the connection of an image generation unit. The adapter can be connected to the image generation unit by the interface on the image side. A cable is preferably connectable to the interface on the image side, so that the output signals from the image sensor are transmittable to the adapter and/or the control signals are transmittable from the adapter to the image generation unit/image sensor/further sensor via the cable. Alternatively, however, the interface on the image side can also be configured as a wireless interface, as explained above.

According to one particularly advantageous design, it can furthermore be provided that a connection between the image generation unit and the adapter, i.e., in particular, the aforementioned interface on the image side, is mechanically and/or electrically coded. This coding is preferably designed in such a way that only one specific image generation unit type, in particular endoscope type, is connectable to the adapter. The use of the image recording arrangement can therefore be designed on the whole as substantially safer.

A further design of the invention proposes that the adapter is configured to receive and/or transmit electromagnetic waves, i.e., in particular, optical waves or radio waves. In a design of this type, it can be provided, in particular, that the output signals and/or image data from the image sensor and/or the control commands which the camera control unit transmits to the adapter and/or the control signals which the adapter transmits to the image generation unit/image sensor/further sensor are transmittable in each case by a wireless link.

A transceiver unit can preferably be configured in or on the adapter for this purpose. In this case, the adapter performs the role of a wireless access point.

According to further possible designs of the image recording arrangement, the adapter can also be configured to set up a plurality of separate data connections, in particular at least one wired and/or at least one wireless data connection, between the image generation unit and the camera control unit.

One further development of the communication apparatus provides that it has a conversion unit for converting data and/or signals. A parallel data transmission, for example, can be converted into a serial data transmission or vice versa by means of the conversion unit. This conversion can furthermore take place in either of the two directions of the bidirectional data connection provided by the adapter. The conversion unit can thus convert data which are transmitted from the image generation unit to the camera control unit and/or data which are transmitted from the camera control unit to the image generation unit.

The conversion unit is preferably configured in such a way that data and/or signals which reach the adapter in at least one first format are transmittable by the adapter in at least one second format differing from said first format. For this purpose, the conversion unit can be formed, in particular, by a microprocessor or a field programmable gate array (FPGA) or other integrated circuit.

With the image recording arrangement, different data formats are furthermore exchangeable between one image generation unit or different image generation units and the camera control unit. The conversion unit can, for example, be configured in multiple fashion for this purpose. The adapter can thus, in particular, have a plurality of conversion units which are preferably disposed in parallel with one another in the signal flow and are configured in each case for the conversion from a first data format into a second data format. The conversion units can be implemented, for example, by use of microprocessors disposed in parallel in the signal flow.

It is furthermore preferable if the conversion unit is defined in terms of its electronic characteristics specifically for the image sensor and for the further sensor and/or for the camera control unit.

Finally, it can be provided that the electronic characteristics of the conversion unit are invariable.

One development of the adapter according to the invention provides that said adapter configures a galvanic isolation. This galvanic isolation can be implemented, in particular, between the image generation unit and the camera control unit and/or between the image generation unit and a cable connected to the camera control unit and/or between the camera control unit and a cable connected to the image generation unit.

In one specific design of the image recording arrangement discussed here, it is provided that the adapter is configured to set up a further data connection between the camera control unit and a further image sensor of a further image generation unit. It is highly advantageous here if the adapter is also arrangeable at a distance from the further image generation unit and is thus removable from a further sterile area of the further image generation unit.

According to one particularly advantageous design, image data from the further image sensor of the further image generation unit are also transmittable via the data interface already described above to the camera control unit. A user can thus, for example, display the image signals from a plurality of endoscopes connected to the adapter on the camera control unit using an adapter of this type.

The camera control unit can be configured accordingly to process and/or display image data from the image sensor and from a further image sensor and/or from a further sensor. It is preferable here if these image data and/or other data from the further sensor are transmitted via the data interface of the adapter to the camera control unit.

In a further design, it is provided that the adapter is configured for the further processing of, in particular analog, image data which are obtained from the output signals from the image sensor. To do this, the adapter can have an image processing unit and/or storage memory for the temporary storage of image data.

The image sensor and/or the further sensor of the image generation unit can produce analog or digital output signals. It can be provided accordingly that the adapter is configured to process analog and/or digital output signals from the image sensor and/or from a further sensor. It is advantageous that the output signals no longer have to be processed in the image generation unit. The image generation unit can therefore be designed as free from memory and/or free from an image processing unit.

In addition, the image generation unit can also be designed as free from shielding. In this case, it is preferable if a shielding from electromagnetic interference is configured inside the adapter or on the adapter.

In order to further increase the user-friendliness of the image recording arrangement, it can be provided, in particular, that the camera control unit is configured for the, preferably automated, setting of the data connection. This can preferably take place in such a way that a user does not have to reset the data connection on the adapter even if the image generation unit is exchanged, but can set it instead by the camera control unit. Alternatively or additionally, the data connection is also settable in an automated manner by means of the camera control unit.

It can be provided, for example, that the communication apparatus is reprogrammable by a user and/or by the camera control unit itself in an automated manner via the camera control unit and the interface described above. The user can thus easily define the adapter according to the invention via operating elements of the camera control unit specifically for an image generation unit to be used with the adapter.

The following designs can also be provided for the expedient configuration of the image recording arrangement:

The adapter can, for example, have an interface for the input of electrical power and/or a light source for the emission of light, in particular illumination or excitation light, or an element for the conduction of light. It can be advantageous here if the adapter has a light conductor connection via which light is transmittable to the image generation unit. However, the adapter can also have an illumination unit which supplies light, for example using a light conductor, to the distal end of the image generation unit. Alternatively, an optical conduction can also be configured on the adapter, so that light provided from an external illumination source (for example disposed in the camera control unit) is forwardable through the adapter to the image generation unit.

By use of a sufficiently long cable and/or using a transceiver unit with sufficiently high transceiver power, the adapter can be designed in such a way that the data connection between the image sensor/image generation unit and the camera control unit can be set up if the adapter is located outside the sterile area of the image generation unit. The adapter is furthermore preferably designed so that it is non-destructively disconnectable from the image generation unit if the data connection is interrupted.

The features of the subsidiary, usage-oriented claim are provided according to the invention for a use of an image recording arrangement of the aforementioned type in order to achieve the aforementioned object. According to the invention, it is thus proposed, in particular, that an image recording arrangement, comprising an image generation unit with an image sensor, a camera control unit and an adapter for setting up a bidirectional data connection between the image sensor and the camera control unit, is used in such a way that the adapter is connected successively to a plurality of image generation units of the same type, in particular a plurality of single-use endoscopes of the same type. The image recording arrangement can be designed here, in particular, as described above and/or according to one of the claims oriented toward an image recording arrangement.

In the case of a use of this type, the adapter is thus used multiple times in succession, whereas the image generation unit is exchanged in each case following a single use. The same camera control unit can also be used here.

A further use according to the invention of an image recording arrangement of the aforementioned type provides that the adapter sets up a data connection to the camera control unit simultaneously for a plurality of image generation units, in particular a plurality of single-use endoscopes which in each case have an image sensor. With this method, a plurality of image generation units are therefore simultaneously controllable via the adapter and/or image signals can be transmitted simultaneously from a plurality of image sensors to the camera control unit. The camera control unit is therefore preferably used for the simultaneous display of image data from the plurality of image generation units. For this purpose, the circuitry of the adapter can, in particular, be designed specifically for use with the image sensors of the plurality of image generation units and/or with the camera control unit. It is preferable in the case of uses of this type also if the image recording arrangement is designed as described above and/or according to one of the claims oriented toward an image recording arrangement.

In the case of a use of an image recording arrangement as described above, it can be provided, in particular, according to the invention that the plurality of image generation units are of at least two different types and/or that the adapter sets up at least two separate data connections. Here, the two separate data connections can, in particular, be designed in each case specifically for one of the at least two types.

The features of the method are furthermore provided according to the invention in order to achieve the aforementioned object. In particular, it is thus provided according to the invention, in order to achieve the object in a method for commissioning an image recording arrangement of the type described above which can be designed, in particular, as described above and/or according to one of the claims oriented toward an image recording arrangement, that the following steps are carried out, preferably in the indicated sequence:

Step 1: Define the adapter specifically for use with a specific type of image generation unit and/or image sensor and/or further sensor;

Step 2: Set up a connection between the adapter and the camera control unit;

Step 3: Set up a bidirectional data connection between the camera control unit and the image generation unit/image sensor/further sensor by the adapter.

In this method, unlike previously known methods, it can thus be provided that no identification information is transmitted from the adapter to the camera control unit either before or during or after the set-up of the bidirectional data connection. This results in a greater safety in the commissioning and subsequent use of the image recording arrangement.

An image recording module is furthermore provided to achieve the aforementioned object. The image recording module comprises at least two different image recording units, at least two different adapters and a camera control unit. The image recording module is characterized in that each of the at least two different image generation units is assigned in each case to one of the at least two different adapters, wherein an image recording arrangement as described above or according to one of the claims oriented toward an image recording arrangement can be formed from each of the at least two different image generation units with the respective assigned adapter and the camera control unit.

At least two image recording arrangements can thus be configured with the image recording module using the same camera control unit. Here, the at least two different image recording arrangements can differ from one another, for example, in terms of their respective adapters and/or respective image generation units and/or respective image sensors and/or respective further sensors. A wide variety of possible applications of image recording arrangements according to the invention are thus provided using a common camera control unit.

Due to the adapters designed in each case according to the invention, the common camera control unit is thus usable in each of the at least two different image recording arrangements. Due to the provision of a plurality of adapters, in each case defined specifically in advance for a specific image generation unit, the common camera control unit is usable in a versatile manner without the need to provide a complex and therefore expensive universal adapter which is usable with a multiplicity of different image generation units.

One example of an image recording module according to the invention comprises two or more different endoscopes which are use or are usable with an adapter according to the invention designed specifically for the respective endoscope and having a single common camera control unit.

Finally, an image recording series is provided to solve the aforementioned object. This comprises at least two different image recording arrangements which are configured in each case as described above or according to one of the claims oriented toward an image recording arrangement, and is characterized in that the camera control units of the at least two different image recording arrangements are configured identically.

In an image recording series of this type also, the at least two different image recording arrangements of the series can differ from one another in terms of their respective adapters and/or respective image generation units and/or respective image sensors and/or respective further sensors.

BRIEF DESCRIPTION OF THE DRAWINGS

The invention will now be described in detail with reference to example embodiments, but is not restricted to these example embodiments.

Further example embodiments can be derived by combining the features of individual or a plurality of claims with one another and/or with individual or a plurality of features of the respective example embodiment combination. In particular, configurations of the invention can thus be obtained from the following description of a preferred example embodiment in conjunction with the general description, the claims and the drawings.

In the drawings:

Figure 1:
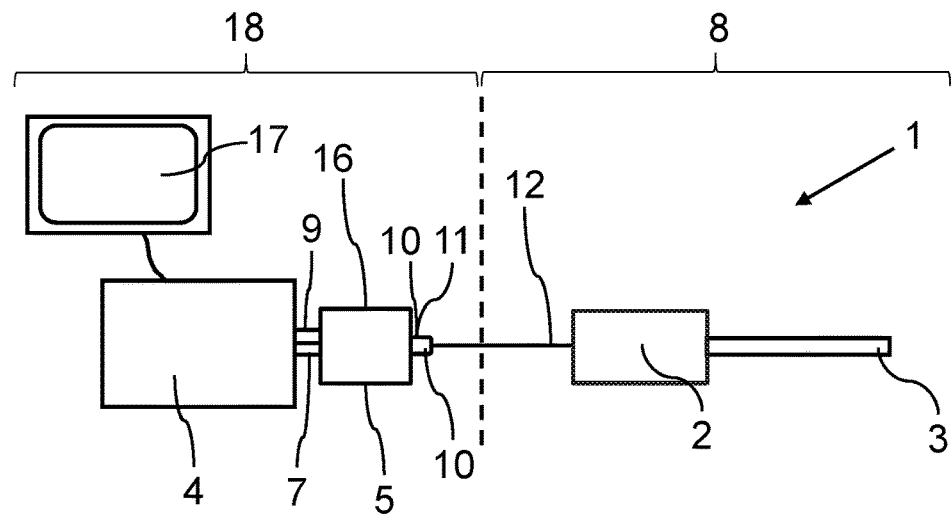
Figure 2:
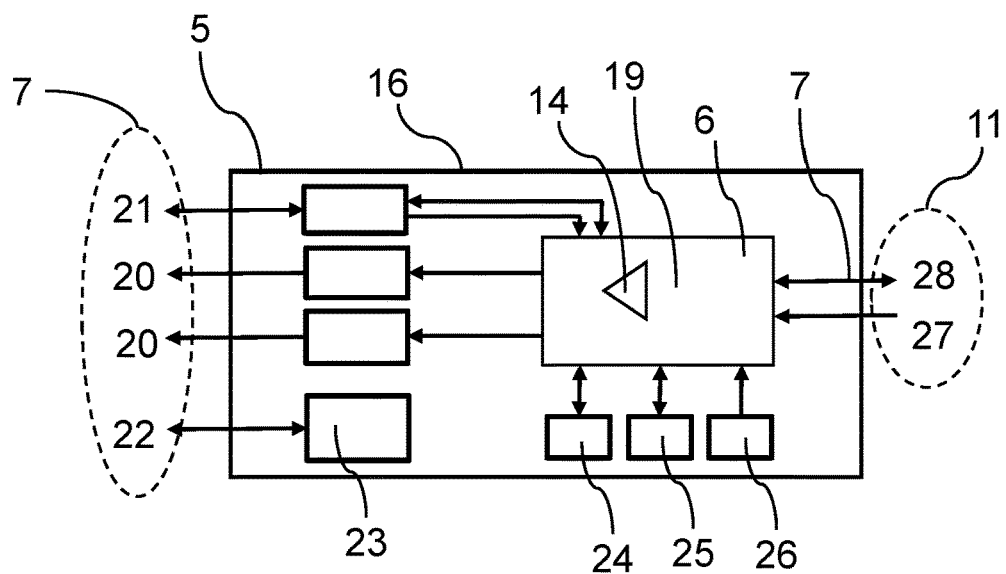
Figure 3:
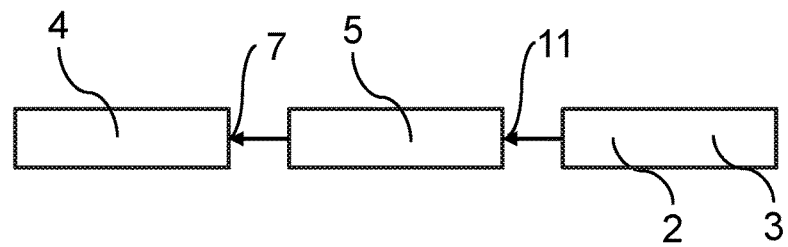
Figure 4:
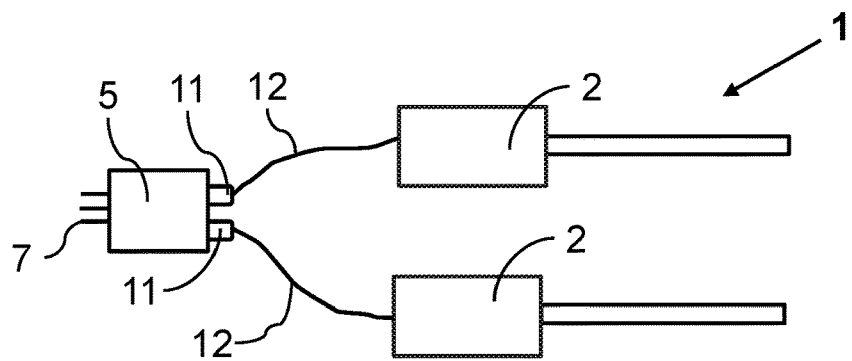
Figure 5:
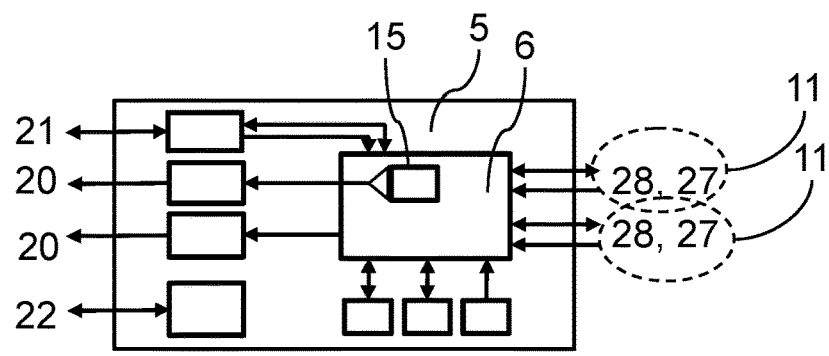
Figure 6:
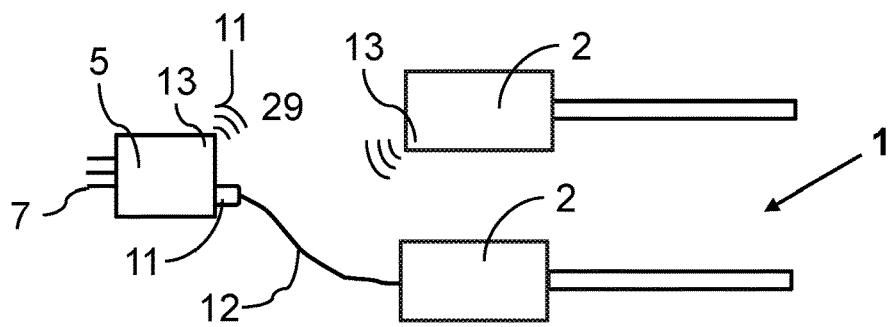
Figure 7:
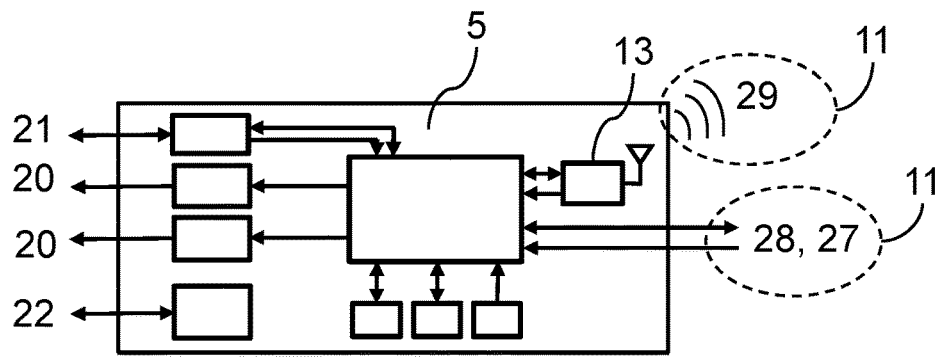
Figure 8:
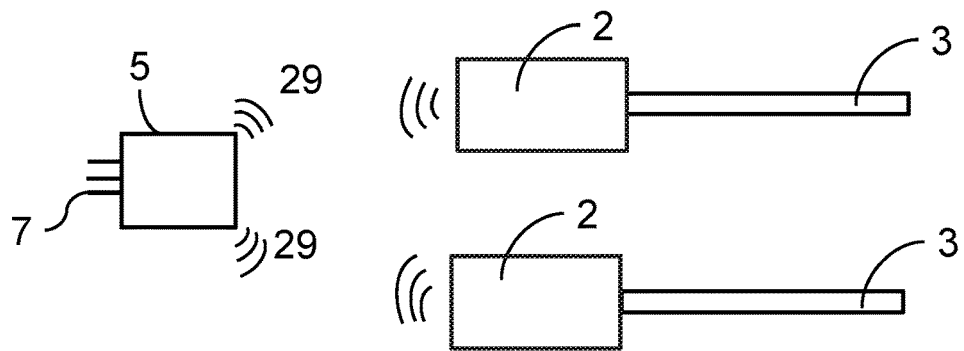
Figure 9:
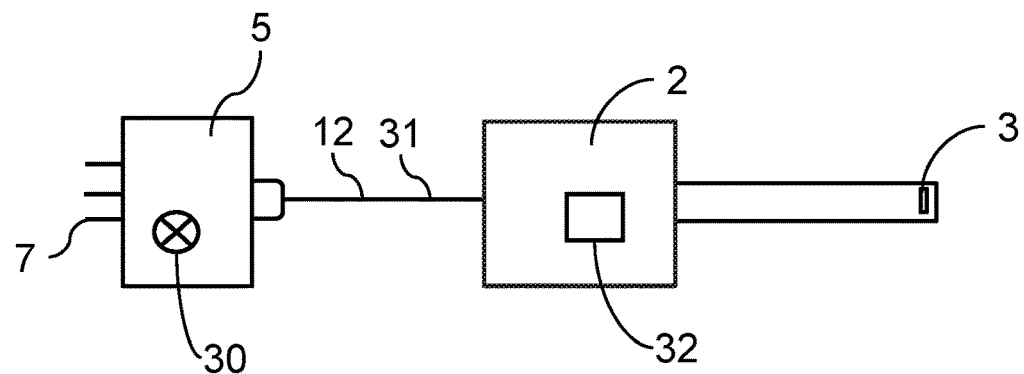
Figure 10:
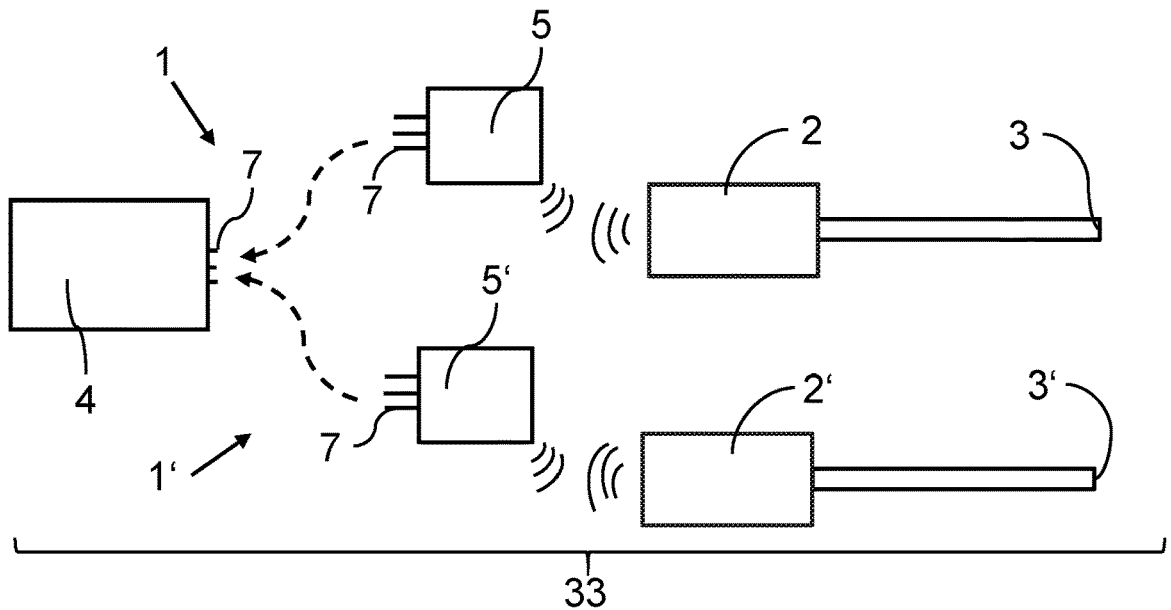

FIG. 1 shows a schematic overview of an image recording arrangement according to the invention, FIG. 2 shows schematically the internal structure of an adapter designed according to the invention, FIG. 3 shows a flow diagram which illustrates the signal flow from the image sensor to the camera control unit, FIG. 4 shows the use of two endoscopes jointly with one adapter according to the invention, FIG. 5 shows the internal structure of the adapter from FIG. 4, FIG. 6 shows the operation of two endoscopes using an adapter according to the invention which has both a wired and a wireless interface, FIG. 7 shows the internal structure of the adapter from FIG. 6, FIG. 8 shows the use of two endoscopes which are connected in each case by means of a wireless link to the adapter according to the invention, FIG. 9 shows the use of an adapter according to the invention which has a light source, and FIG. 10 shows an image recording module according to the invention.

DETAILED DESCRIPTION

In order to explain the invention, FIG. 1 shows a highly schematic representation of an image recording arrangement denoted in its entirety as 1. This consists of an endoscope 2 which has a distally disposed image sensor 3 and acts as an image generation unit 2. The endoscope 2 is connected by a cable 12 to an adapter 5 via an interface 11 on the image side configured as a plug-in connection 10. The adapter 5 is in turn inserted into a camera control unit 4 by means of a further plug-in connection 9, wherein a data interface 7 is configured between the camera control unit 4 and the adapter 5 by this plug-in connection. The camera control unit 4 has a monitor 17 to display the image data from the image sensor 3. The adapter 5 has a shielding 16 to suppress electromagnetic interference sources.

The adapter 5 sets up a bidirectional data connection between the image sensor 3 and the camera control unit 4. On the one hand, analog output signals generated by the image sensor 3 are transmitted via the cable 12 to the adapter 5 which converts the output signals into digital image or video data and transmits these image/video data via the data interface 7 to the camera control unit 4. On the other hand, the camera control unit 4 transmits control and adjustment commands to the adapter 5 via the data interface 7, wherein said adapter converts the control and adjustment commands into control signals readable by the image sensor 3 and transmits them via the cable 12 to the image sensor 3.

Due to the length of the cable 12, the adapter 5 can be removed from a sterile area 8 of the endoscope 2 into a non-sterile area 18 while the data connection is maintained. The adapter 5 can therefore remain disposed outside the sterile area 8 even when the data connection is being set up, but also during the operation of the endoscope 2.

As shown in FIG. 2, in order to configure the bidirectional data connection, the adapter 5 has a communication apparatus 6 with which control signals can be transmitted to the image sensor 3 and output signals from the image sensor 3 can be received. In the same way, the communication apparatus 6 can also transmit control signals to further sensors (not shown) which are located, for example, in the distal end area of the endoscope 2.

In the exemplary embodiment shown, the communication apparatus 6 is formed by an FPGA 19 which communicates with the camera control unit 4 via a control and adjustment output 28 and a video input 27 with the endoscope 2 and by the use of a serial interface 21, a bidirectional data interface 22 and two digital video outputs 20. As the dotted line in FIG. 2 indicates, the four last-named interfaces form the data interface 7 according to the invention between the adapter 5 and the camera control unit 4, while the interface 11 on the image side for controlling the endoscope 2 and the image sensor 3 is formed by the video input 27 and the control and the control and adjustment output 28.

The adapter 5 according to the invention shown in FIG. 2 furthermore has a random access memory (RAM) 24, a flash memory 25 and an open sound control (OSC) interface which can be controlled or read in each case by the FPGA 19. The camera control unit 4 can furthermore read a read only memory (ROM) 23 via the bidirectional data interface 22 and can thus recognize the type of the adapter 5.

The camera control unit 4 can, in principle, also access, control and adjust the FPGA 19 and therefore the communication apparatus 6 by the serial interface 21; in particular, a reprogramming of the communication apparatus 6, for example in order to define the adapter 5 specifically for use with a quite specific endoscope type, can be performed via this interface. The user can easily carry out a reprogramming of this type via operating elements on the communication apparatus 6.

As shown schematically in FIG. 3, in the image recording arrangement 1 according to the invention illustrated in FIG. 1, analog output signals from the image sensor 3 are first transmitted from the endoscope 2 via the interface 11 on the image side to the adapter 5. A signal conversion takes place in the adapter 5, wherein the output signals are converted into a format readable by the camera control unit 4. This conversion comprises, in particular, an analog-to-digital conversion.

The communication apparatus 6 has a conversion unit 14 (shown in FIG. 2 only) to carry out this conversion. The converted data are transmitted from the adapter 5 via the digital data interface 7 to the camera control unit 4. An image processing, in particular, can then take place in the camera control unit 4. However, it can also be provided according to the invention that an image processing already takes place in the adapter 5 and the adapter 5 has an image processing unit 15 for this purpose, as shown in FIG. 5.

FIG. 4 shows that an adapter 5 according to the invention can be configured, in particular, to set up two separate bidirectional data connections. The adapter 5 shown in FIG. 4 thus has two interfaces 11 on the image side via which an endoscope 2 can be connected in each case by a cable 12 to the adapter 5.

Correspondingly, as shown in FIG. 5, the adapter 5 from FIG. 4 in each case has two control and adjustment outputs 28 and two video inputs 27. Apart from the additionally provided image processing unit 15, the adapter 5 is otherwise designed in a similar manner to the adapter 5 shown in FIG. 2.

FIG. 6 in turn shows a further example embodiment of an image recording arrangement 1 according to the invention. Here, in addition to a first interface 11 on the image side with which a first endoscope 2 is connected via a cable connection to the adapter 5, the adapter 5 has a transceiver unit 13. A wireless link 29 can be set up with said transceiver unit to a second endoscope 2 which similarly has a transceiver unit 13.

The corresponding design of the adapter 5 from FIG. 6 is shown in FIG. 7, in particular the transceiver unit 13 disposed inside the adapter 5 with which a second interface 11 on the image side can be configured.

Finally, in the exemplary embodiment shown in FIG. 8, two endoscopes 2 which in each case have an image sensor 3 can in each case transmit image data via a separate wireless link 29 to the adapter 5 which converts these two image data streams and transmits them via a data interface 7 to a downstream camera control unit 4.

FIG. 9 shows that an adapter 5 according to the invention can have a light source 30 from which light can be transmitted via an optical fiber 31 to an endoscope 2. In addition, it is also possible for the endoscope 2 of the image recording arrangement 1 to have a processor 32, for example an IC bridge processor, with which, in particular, an image editing or image processing can already be carried out in the endoscope 2.

The method according to the invention for commissioning an image recording arrangement can also be clearly explained with reference to FIG. 1. In contrast to conventional practice in the prior art, no information relating to the endoscope 2 currently to be used or the image sensor 3 to be used needs to be stored in the camera control unit 4. Instead, it suffices that a standardized communication between the camera control unit 4 and the adapter 5 is defined via the data interface 7.

Since the adapter 5 is defined according to the invention specifically for use with a specific endoscope type or a specific image sensor type, or is definable specifically for such a type via the "interface for reprogramming the communication apparatus 6" described above, in particular before the bidirectional data connection is set up, it suffices if the camera control unit 4 transmits control and/or adjustment commands to the adapter 5, said control and/or adjustment commands being processable by the latter. The adapter 5 according to the invention thus performs the translation of these commands into control signals readable by the image sensor 3/endoscope 2. In the opposite communication direction, the adapter 5 translates output signals from the image sensor 3 or other readable characteristics from the endoscope 2, for example output signals from a further sensor disposed in the endoscope head, into data which are transmitted via the standardized data interface 7 to the camera control unit 4 and are processed by the latter.

Correspondingly, the method according to the invention provides that the adapter 5 is defined in a first step, even before the adapter 5 is connected to the endoscope 2 of the image recording arrangement 1, specifically for use with the type of the endoscope 2/the type of the image sensor 3 of the image recording arrangement 1. This specific definition (step 1) can already take place, for example, during the manufacture of the adapter 5 and may, in particular, no longer be modifiable; or it takes place via the interface described above and is performed by a user during the commissioning of the image recording arrangement 1.

The adapter 5 can already be connected to the camera control unit with the endoscope 2 in a second step due to this specific definition of the adapter 5.

In a third step, the bidirectional data connection is then configured between the endoscope 2, in particular its image sensor 3, and the camera control unit 4. The adapter must obviously be connected to the endoscope for this purpose, wherein this connection can be set up before or after the connection of the adapter to the camera control unit.

No information relating to the endoscope 2/image sensor 3 or further sensor to be used needs to be transmitted to the camera control unit 4 in order to set up the bidirectional data connection. The camera control unit 4 can therefore control and/or adjust the endoscope 2 and/or the image sensor 3 and/or can receive image data from the endoscope 2 immediately and/or without knowledge of the endoscope 2 actually connected to the adapter 5 and/or without specific adaptation to the endoscope 2/image sensor 3.

Finally, FIG. 10 illustrates the use or design of an image recording module 33 according to the invention. This consists of two different image recording arrangements 1 and 1' which differ from one another in terms of the endoscope 2 or 2' used in each case or the image sensor 3/3' used in each case in the endoscope 2/2' (cf. FIG. 10). Each of the image recording arrangements 1 and 1' comprises a respective adapter 5 or 5' which is defined in advance specifically for the image sensor 3 or 3' of the respective endoscope 2/2' or is at least specifically definable in advance via the camera control unit 4 used jointly in both image recording arrangements 1 and 1'. As indicated by the dotted lines in FIG. 10, each of the two image recording arrangements 1 and 1' uses the common camera control unit 4. In other words, the image recording arrangement 1 is formed by the camera control unit 4, the endoscope 2 and the adapter 5, while the image arrangement 1' is formed by the camera control unit 4, the endoscope 2' and the adapter 5'.

A user of an image recording module 33 of this type can extend the latter as required by adding further image generation units 2 in each case having an adapted adapter 5, wherein said user can always use the common camera control unit 4 of the image recording module 33 in all respectively manufacturable image recording arrangements 1. This shows the versatility and also the possible cost savings of the concept.

If the image recording module 33 shown in FIG. 10 were extended with a further camera control unit 4 designed identically to the camera control unit 4 shown in FIG. 10, an image recording series within the meaning of the invention would thus be obtained. This series would thus have two image recording arrangements 1 which differ from one another only in terms of the endoscopes and associated adapters that are used, wherein the respective camera control units 4 are configured in a totally identical manner. A series approach of this type also cuts development costs for the camera control unit 4 and thus contributes to the cost reduction of the individual image recording arrangements 1.

To summarize, in order to reduce the costs of endoscopic examinations and enable new operating concepts, an image recording arrangement 1 is proposed in which an adapter 5 enables a bidirectional communication between a camera control unit 4 and an image generation unit 2 which has an image sensor 3. To do this, a standardized data interface 7 is configured between the camera control unit 4 and the adapter 5, wherein the adapter 5 is defined or is at least definable specifically for use with a specific type of image generation unit. For this purpose, the adapter 5 has a communication apparatus 6 which translates control and adjustment commands transmitted by the camera control unit 4 into a format processable by the image generation unit 2 and provides image data from the image sensor 3 in a format processable by the camera control unit 4. The camera control unit 4 can therefore access, control and adjust the image generation unit 2 without adaptation to the image generation unit 2 connected to the adapter 5 and therefore without knowledge of said image generation unit, and can display image data from the image generation unit 2 (cf. FIG. 1).

REFERENCE NUMBER LIST

1 Image recording arrangement
2 Image generation unit (e.g. endoscope)
3 Image sensor
4 Camera control unit
5 Adapter
6 Communication device
7 Data interface
8 Sterile area
9 First plug-in connection
10 Second plug-in connection
11 Interface on the image side 12 Cable
13 Transceiver unit
14 Conversion unit
15 Image processing unit
16 Shielding
17 Monitor
18 Non-sterile area
19 Field programmable gate array (FPGA)
20 Video output
21 Serial interface (COM)
22 Bidirectional data interface
23 Read only memory (ROM)
24 Random access memory (RAM)
25 Flash memory
26 Open sound control interface (OSC)
27 Video input
28 Control and adjustment output
29 Wireless link
30 Light source
31 Optical fiber
32 Processor
33 Image recording module

The invention claimed is:

1. An image recording module (33) with at least one image generation unit (2), at least one electronic adapter (5) and a camera control unit (4), each of the at least one image generation units (2) is assigned in each case to one of the at least one electronic adapters (5), and each of the at least one image generation units (2) with the respective assigned electronic adapter (5) and the camera control unit (4) form an image recording arrangement (1), wherein:
each said image generation unit (2) includes at least one image sensor (3),
each said electronic adapter (5) is defined for connection with a specific type of image generation unit and configured to set up a bidirectional data connection between the image sensor (3) and the camera control unit (4) by forming an interface (11) on an image side and a data interface (7) on an opposite side,
each said electronic adapter (5) includes a communication apparatus (6) for transmitting control signals to the image sensor (3) and for receiving output signals from the image sensor (3),
the communication apparatus (6) is already defined specifically for the image sensor (3) before a connection is first set up between the respective electronic adapter (5) and the camera control unit (4), wherein the communication apparatus (6) includes a conversion unit (14) that is configured to convert at least one of data or signals, such that the at least one of the data or signals which reach the respective electronic adapter (5) in a first format are transmittable by said respective electronic adapter (5) in a second format differing from said first format, and
each said electronic adapter (5) is non-destructively disconnectable from the image generation unit (2) upon the data connection being interrupted, such that the camera control unit (4) is adaptable to a new image generation unit through exchange of the adapter (5) or through defining the electronic adapter (5) for connection with the new image generation unit by reprogramming the communication apparatus (6) of the adapter (5) via an interface.

2. The image recording module (33) as claimed in claim 1, wherein the image generation units (2) each have at least one further sensor selected from a group consisting of a pressure sensor, a temperature sensor, or a position sensor, and the communication apparatus (6) is configured to transmit control signals to the at least one further sensor and to receive output signals or data from the at least one further sensor.

3. The image recording module (33) as claimed in claim 2, wherein at least one of: each said electronic adapter (5) has an interface for reprogramming the communication apparatus (6), or the image generation unit each comprise an endoscope (2) that is a single use or non-autoclavable single-use endoscope (2).

4. The image recording module (33) as claimed in claim 2, wherein the image recording arrangement (1) is configured such that the camera control unit (4) has a controlling/adjusting effect on at least one of the image generation unit (2), the image sensor (3), or the at least one further sensor as soon as the adapter (5) sets up the data connection, without knowledge of the respective one or more of the image generation unit (2), the image sensor (3), or the at least one further sensor then connected to the adapter (5).

5. The image recording module (33) as claimed in claim 2, wherein the communication apparatus (6) includes electronic characteristics specifically for at least one of the reception of output signals from a specific image sensor type or the generation of control signals for a specific image generation unit, or at least one of the image generation unit (2), the image sensor (3), or the further sensor is usable as intended only together with the adapter (5).

6. The image recording module (33) as claimed in claim 2, wherein each said electronic adapter (5) has a data interface (8) for receiving control commands transmitted by the camera control unit (4) and for transmitting image data from at least one of the image sensor (3) or other data from the further sensor to the camera control unit (4) in a format processable by the camera control unit (4).

7. The image recording module (33) as claimed in claim 2, wherein each said electronic adapter (5) is arrangeable at a distance from the image generation unit (2) and is removable from a sterile area (8) of the image generation unit (2) while the data connection is maintained.

8. The image recording module (33) as claimed in claim 2, wherein each said adapter (5) has an interface (11) on an image side, provided as a second plug-in connection (10), for connection of the image generation unit (2), so that at least one of the output signals or the control signals are transmittable via a cable (12) to the image generation unit (2), or a connection between the image generation unit (2) and the adapter (5) is at least one of mechanically or electrically coded such that only one specific image generation unit type is connectable to the adapter (5).

9. The image recording module (33) as claimed in claim 2, wherein each said adapter (5) is configured to at least one of receive or transmit electromagnetic waves such that at least one of the output signals or image data from the image sensor (3), or at least one of the control commands or the control signals are transmittable in each case via a wireless link.

10. The image recording module (33) as claimed in claim 2, wherein the conversion unit (14) comprises a microprocessor or FPGA or other integrated circuit, and the conversion unit (14) is defined in terms of its electronic characteristics for at least one of the image sensor (3), the further sensor, or the camera control unit (4).

11. The image recording module (33) as claimed in claim 1, wherein each said adapter (5) configures a galvanic isolation between the image generation unit (2) and the camera control unit (4) and between the image generation unit (2) and a cable (12) connected to the camera control unit (4) and between the camera control unit (4) and a cable (12) connected to the image generation unit (2).

12. The image recording module (33) as claimed in claim 1, wherein each said electronic adapter (5) is configured to set up a further data connection between the camera control unit (4) and a further image sensor (3') of a further image generation unit (2), and each said electronic adapter (5) is also arrangeable at a distance from the further image generation unit (2') and is removable from a further sterile area (8') of the further image generation unit (2').

13. The image recording module (33) as claimed in claim 2, wherein the camera control unit (4) is configured to at least one of process or display image data from the image sensor (3) and from a further image sensor (3') or from the further sensor, and the at least one of the image data or other data from the further sensor are transmitted via the data interface (7) of each said electronic adapter (5) to the camera control unit (4).

14. The image recording module (33) as claimed in claim 2, wherein each said electronic adapter (5) is configured for the further processing of the image data obtained from the output signals from the image sensor (3), and each said electronic adapter (5) has at least one of an image processing unit (15) or a storage memory for the temporary storage of image data for this purpose.

15. The image recording module (33) as claimed in one of claim 2, wherein each said electronic adapter (5) is configured for the processing of at least one of analog or digital output signals from at least one of the image sensor (3) or from the further sensor, and the respective image generation unit (2) is free from at least one of: storage memory, an image processing unit (15), or shielding.

16. The image recording module (33) as claimed in claim 2, wherein the camera control unit (4) is configured for setting of the data connection, such that a user does not have to reset the data connection on the respective electronic adapter (5) even if the image generation unit (2) is exchanged, and is instead settable by the camera control unit (4).

17. A method of using the image recording module (33) according to claim 1, the method including:
connecting one said electronic adapter (5) successively to a plurality of the image generation units (2) of a same type including a plurality of single-use endoscopes (2) of the same type.

18. A method of using the image recording module (33) according to claim 1, the method including:
one said electronic adapter (5) setting up a data connection to the camera control unit (4) simultaneously for a plurality of image generation units (2) which in each case have an image sensor (3), and
simultaneously displaying image data with the camera control unit (4) from the plurality of image generation units (3).

19. A method for commissioning an image recording arrangement (1), the method comprising:
providing the image processing arrangement including an image generation unit (2) with at least one image sensor (3), a camera control unit (4), a separate, exchangeable electronic adapter (5) defined for connection with a specific type of image generation unit and configured to set up a bidirectional data connection between the image sensor (3) and the camera control unit (4) by forming an interface (11) on an image side and a data interface (7) on an opposite side, the adapter (5) includes a communication apparatus (6) for transmitting control signals to the image sensor (3) and for receiving output signals from the image sensor (3), the communication apparatus (6) is already defined specifically for the image sensor (3) before a connection is first set up between the adapter (5) and the camera control unit (4), and the adapter (5) is non-destructively disconnectable from the image generation unit (2) upon the data connection being interrupted, such that the camera control unit (4) is adaptable to a new image generation unit through exchange of the adapter (5),
defining the electronic adapter (5) specifically for connection with at least one of a specific type of the image generation unit (2), the image sensor (3) or a further sensor;
setting up a connection between the electronic adapter (5) and the camera control unit (4); and
setting up a bidirectional data connection between the camera control unit (4) and at least one of the image generation unit (2), the image sensor (3), or the further sensor,
wherein the defining of the electronic adapter (5) is performed via an interface for reprogramming the communication apparatus (6) of the adapter (5) by a user during commissioning of the image recording arrangement (1).

20. A method for commissioning an image recording arrangement (1), the method comprising:
providing the image processing arrangement including an image generation unit (2) with at least one image sensor (3), a camera control unit (4), a separate, exchangeable electronic adapter (5) defined for connection with a specific type of image generation unit and configured to set up a bidirectional data connection between the image sensor (3) and the camera control unit (4) by forming an interface (11) on an image side and a data interface (7) on an opposite side, the adapter (5) includes a communication apparatus (6) for transmitting control signals to the image sensor (8) and for receiving output signals from the image sensor (8), the communication apparatus (6) is already defined specifically for the image sensor (8) before a connection is first set up between the adapter (5) and the camera control unit (4), wherein the communication apparatus (6) includes a conversion unit (14) that is configured to convert at least one of data or signals, such that the at least one of the data or signals which reach the respective electronic adapter (5) in a first format are transmittable by said respective electronic adapter (5) in a second format differing from said first format, and the adapter (5) is non-destructively disconnectable from the image generation unit (2) upon the data connection being interrupted, such that the camera control unit (4) is adaptable to a new image generation unit through exchange of the adapter (5), wherein the defining of the electronic adapter (5) is performed via an interface for reprogramming the communication apparatus (6) of the adapter (5) by a user during commissioning of the image recording arrangement (1),
defining the electronic adapter (5) specifically for connection with at least one of a specific type of the image generation unit (2), the image sensor (3) or a further sensor;
setting up a connection between the electronic adapter (5) and the camera control unit (4); and
setting up a bidirectional data connection between the camera control unit (4) and at least one of the image generation unit (2), the image sensor (3), or the further sensor, wherein the camera control unit (4) is adapted to a new image generation unit (2) by exchanging the electronic adapter (5).

\* \* \* \* \*